(12) United States Patent
Cheng et al.

(10) Patent No.: US 11,559,690 B2
(45) Date of Patent: Jan. 24, 2023

(54) VENTRICULAR ASSIST SYSTEM AND METHOD

(71) Applicant: Medtronic, Inc., Minneapolis, MN (US)

(72) Inventors: Alan Cheng, Minneapolis, MN (US); Jian Cao, St. Paul, MN (US); Hai Huang, St. Paul, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 9 days.

(21) Appl. No.: 17/219,510

(22) Filed: Mar. 31, 2021

(65) Prior Publication Data

US 2021/0339020 A1 Nov. 4, 2021

Related U.S. Application Data

(60) Provisional application No. 63/017,722, filed on Apr. 30, 2020.

(51) Int. Cl.
*A61N 1/00* (2006.01)
*A61N 1/362* (2006.01)
*A61N 1/05* (2006.01)
*A61N 1/36* (2006.01)

(52) U.S. Cl.
CPC ............. *A61N 1/3629* (2017.08); *A61N 1/05* (2013.01); *A61N 1/36042* (2013.01)

(58) Field of Classification Search
None
See application file for complete search history.

(56) References Cited

U.S. PATENT DOCUMENTS

| | | | |
|---|---|---|---|
| 4,014,317 A | 3/1977 | Bruno | |
| 6,942,672 B2 | 9/2005 | Heilman et al. | |
| 8,771,165 B2 | 7/2014 | Choi et al. | |
| 9,042,979 B2 | 5/2015 | Peters et al. | |
| 9,579,437 B2 * | 2/2017 | LaRose | A61M 60/148 |
| 9,592,327 B2 | 3/2017 | Wariar et al. | |
| 9,968,719 B2 | 5/2018 | Colella | |

(Continued)

FOREIGN PATENT DOCUMENTS

| | | |
|---|---|---|
| DE | 102018107518 | 10/2018 |
| EP | 2249746 | 11/2010 |

OTHER PUBLICATIONS

Transonic, "Know Real Flow in Ventricular Assist Devices (VADs) & Detect Flow Compromise", 2017, 4 pages.

(Continued)

*Primary Examiner* — John R Downey
*Assistant Examiner* — Anant A Gupta
(74) *Attorney, Agent, or Firm* — Shumaker & Sieffert, P.A.

(57) ABSTRACT

Various embodiments of a ventricular assist system and a method of using such system are disclosed. The system includes a pump adapted to be connected to a heart of a patient, an outflow cannula including a first end adapted to be connected to an outlet of the pump and a second end adapted to be connected to an artery of the patient, and an electrode disposed on an outer surface of the outflow cannula and adapted to be disposed adjacent to an exterior wall of the heart. The system further includes a controller electrically connected to the pump and the electrode, where the controller is adapted to provide a pacing signal to the electrode.

20 Claims, 5 Drawing Sheets

(56) References Cited

U.S. PATENT DOCUMENTS

| | | | |
|---|---|---|---|
| 2006/0064159 A1* | 3/2006 | Porter | A61M 1/3661 623/1.24 |
| 2010/0082099 A1* | 4/2010 | Vodermayer | A61M 60/515 600/17 |
| 2011/0224655 A1 | 9/2011 | Asirvatham et al. | |
| 2012/0059459 A1 | 3/2012 | Asirvatham et al. | |
| 2014/0046120 A1* | 2/2014 | Choi | A61M 60/859 600/16 |
| 2017/0296227 A1* | 10/2017 | Osypka | A61F 2/2487 |
| 2018/0345028 A1* | 12/2018 | Aboud | A61N 1/3787 |
| 2019/0290153 A1 | 9/2019 | Zhang | |
| 2019/0336767 A1 | 11/2019 | Klepfer et al. | |
| 2022/0175316 A1* | 6/2022 | Schmid Daners | A61B 5/7207 |

OTHER PUBLICATIONS

International Search Report and Written Opinion for PCT/US2021/029052 dated Jul. 30, 2021, 14 pages.

\* cited by examiner

US 11,559,690 B2

VENTRICULAR ASSIST SYSTEM AND METHOD

CROSS-REFERENCE TO RELATED APPLICATIONS

The present application claims the benefit of U.S. Provisional Application No. 63/017,722, filed Apr. 30, 2020, which is incorporated herein by reference in its entirety.

TECHNICAL FIELD

This disclosure generally relates to a ventricular assist system and a method of using such system.

BACKGROUND

A ventricular assist device (VAD) or system is an implantable blood pump that can assist an impaired heart by pumping blood to support the workload of the heart. A VAD may be coupled along the arterial system, e.g., between a ventricular chamber and an artery, to pump blood from the ventricle into the arterial system. For example, a left ventricular assist device (LVAD) may be coupled between the left ventricle and the ascending or descending aorta. Assistance in pumping blood by a VAD can be provided to a heart failure patient acutely or chronically, as a bridge to heart transplant, as temporary support to allow myocardial recovery, or as a permanent assist device for heart failure patients contraindicated for heart transplant.

Some patients that utilize a VAD may also require a cardiac rhythm management device, such as a pacemaker or an implantable cardioverter defibrillator (ICD), that monitors a patient's heart rhythm and provides electrical stimulation therapy, such as bradycardia pacing, cardiac resynchronization therapy (CRT), anti-tachycardia pacing (ATP), or a cardioversion/defibrillation (CV/DF) shock, in response to detection of an abnormal electrical rhythm. ICDs are generally designed to detect life threatening ventricular tachyarrhythmia and rapidly respond to the detection by preparing for and delivering ATP and/or cardioversion or defibrillation shock(s) to prevent sudden cardiac death. Heart failure patients are at risk of sudden cardiac death due to arrhythmia. ICD implantation in heart failure patients reduces the risk of sudden cardiac death. Patients having both a VAD and an ICD may have improved survival.

SUMMARY

The techniques of this disclosure generally relate to a ventricular assist device or system that can include an outflow cannula having one or more electrodes disposed on an outer surface of the cannula or within the cannula. The one or more electrodes can be disposed adjacent to a heart of a patient when the system is connected to the heart and the outflow cannula is connected to an outflow of a pump of the system and an artery of the patient. One or more of these electrodes can be utilized to provide one or more electrical signals from a controller to the heart. These signals can include any suitable electrical signal such as a pacing signal or a high voltage stimulation signal. Further, one or more electrodes can be utilized to sense one or more electrical signals from the heart and provide such signals to the controller.

In one example, aspects of this disclosure relate to a ventricular assist system that includes a pump adapted to be connected to a heart of a patient, an outflow cannula including a first end adapted to be connected to an outlet of the pump and a second end adapted to be connected to an artery of the patient, and a pacing electrode disposed on an outer surface of the outflow cannula and adapted to be disposed adjacent to an exterior wall of the heart. The system further includes a controller electrically connected to the pump and the pacing electrode, where the controller is adapted to provide a pacing signal to the pacing electrode.

In another example, aspects of this disclosure relate to a method that includes connecting an inflow cannula of a pump to a portion of a heart of a patient, connecting an outlet of the pump to an outflow cannula, and connecting the outflow cannula to an artery of the patient. The method further includes electrically connecting a pacing electrode disposed on an outer surface of the outflow cannula to a controller, disposing the pacing electrode adjacent to an exterior wall of the heart of the patient, and delivering a pacing signal from the controller to the heart of the patient utilizing the pacing electrode.

In another example, aspects of this disclosure relate to an outflow cannula for a ventricular assist system. The outflow cannula includes a first end adapted to be connected to an outlet of a pump of the ventricular assist system and a second end adapted to be connected to an artery of a patient, and first and second pacing electrodes disposed on an outer surface of the outflow cannula and adapted to be disposed adjacent to an exterior wall of the heart. Each of the first and second pacing electrodes are adapted to be electrically connected to a controller. Further, the first pacing electrode is adapted to deliver a first pacing signal from the controller to the heart and the second pacing electrode is adapted to deliver a second pacing signal from the controller to the heart. The outflow cannula further includes a conductor disposed on the outer surface of the outflow cannula or within the outflow cannula and adapted to electrically connect the first and second pacing electrodes to the controller.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
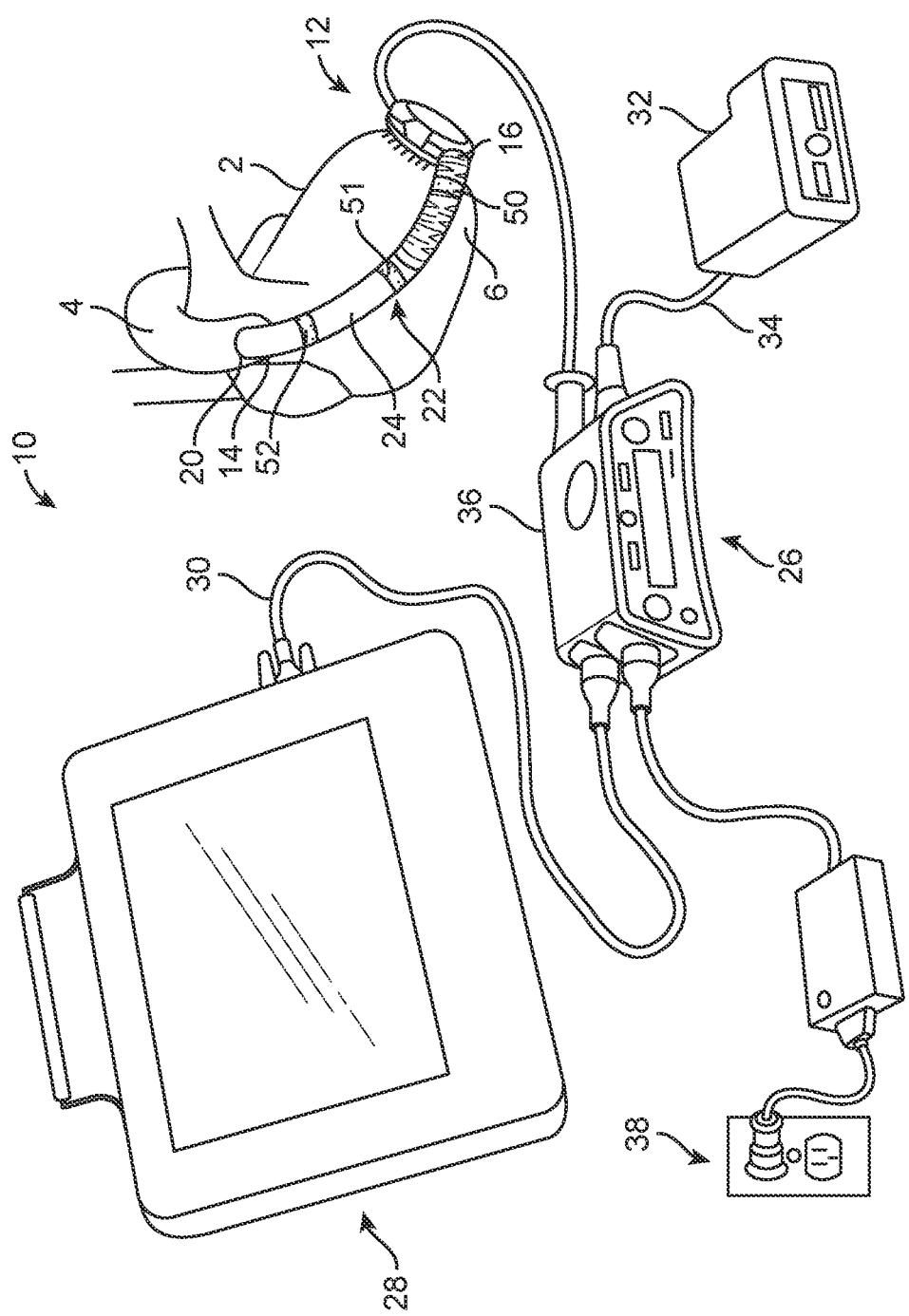
FIG. 1 is a schematic perspective view of one embodiment of a ventricular assist system.

The techniques of this disclosure generally relate to a ventricular assist device or system that can include an outflow cannula having one or more electrodes disposed on an outer surface of the cannula or within the cannula. The one or more electrodes can be disposed adjacent to a heart of a patient when the system is connected to the heart and the outflow cannula is connected to an outflow of a pump of the system and an artery of the patient. One or more of these electrodes can be utilized to provide one or more electrical signals from a controller to the heart. These signals can include any suitable electrical signal such as a pacing signal or a high voltage stimulation signal. Further, one or more electrodes can be utilized to sense one or more electrical signals from the heart and provide such signals to the controller.

Ventricular assist devices (VADs) or systems such as left ventricular assist devices (LVADs) have provided mechanical circulatory support in patients with end stage systolic dysfunction. These devices were predominantly used in patients as bridging therapy to heart transplantation, but now approximately 50% of LVADs are implanted as a destination therapy. LVADs have also evolved over the past 20 years. For example, such devices were initially introduced as pulsatile pumps but have more recently been designed as continuous flow pumps. Continuous flow pumps provide more than 90% of the current market.

Patients who are eligible for LVADs are also at risk for sudden death both from bradyarrhythmias and ventricular tachyarrhythmias because of the severe degree of systolic dysfunction present. Some studies have found that approximately 22-59% of LVAD recipients develop life threatening arrhythmias.

Healthcare providers can, however, be reluctant to implant additional hardware (e.g., implantable medical devices (IMDs) such as implantable cardioverter defibrillators (ICDs) and pacemakers) in patients with VADs due to concerns of increasing the risk for infection. Developing a device that can incorporate electrophysiologic support within the VAD system can prove valuable to both patients and the healthcare system.

One or more embodiments of ventricular assist devices or systems described herein can provide various advantages over currently available systems. For example, one or more embodiments of the systems described herein can include one or more electrodes disposed on an outer surface of an outflow cannula. The one or more electrodes can be disposed adjacent to an exterior wall of a heart of a patient. In one or more embodiments, at least one of the electrodes can be disposed on a pump of the system and adjacent to the exterior wall of the heart. The one or more electrodes can be utilized to provide a signal or signals to the heart. Such signals can include any suitable therapeutic signal or signals. For example, in one or more embodiments, the signal can include one or more pacing signals that can provide treatment to the patient for bradycardia, post-shock pacing, cardiac resynchronization therapy (CRT), anti-tachycardia pacing (ATP), etc. In one or more embodiments, the signals provided to the heart by the one or more electrodes can provide a high voltage stimulation signal to the heart, e.g., for cardioversion/defibrillation (CV/DF) therapy. Further, in one or more embodiments, at least one of the electrodes can sense or detect one or more electrical signals of the heart and provide such signals to a controller of the system.

Placement of the one or more electrodes on at least one of the outflow cannula or the pump of the system can eliminate the need to further implant one or more leads from an IMD such as an ICD or a pacemaker. Instead, one or more signals from the controller can be provided to the heart using the one or more electrodes.

In general, a ventricular assist system can be designed to assist a weakened, poorly functioning left ventricle or other chambers of the heart. In one or more embodiments, the system can include a blood pump that can be implanted, e.g., in a pericardial space of the heart with left ventricular apex to ascending aortic cannulation for left ventricular support. The pump can include any inflow cannula that is separate from or integral with the pump, and an outlet that can be connected to an outflow cannula or graft. A driveline can connect the pump to an external controller. In one or more embodiments, the controller can be implanted within the patient and electrically connected to the pump with an implanted driveline. The controller can be adapted to regulate pump function and monitor the system. Further, the controller can be adapted to provide one or more therapies to the patient's heart using any suitable technique or techniques as is further described herein.

Figure 2:
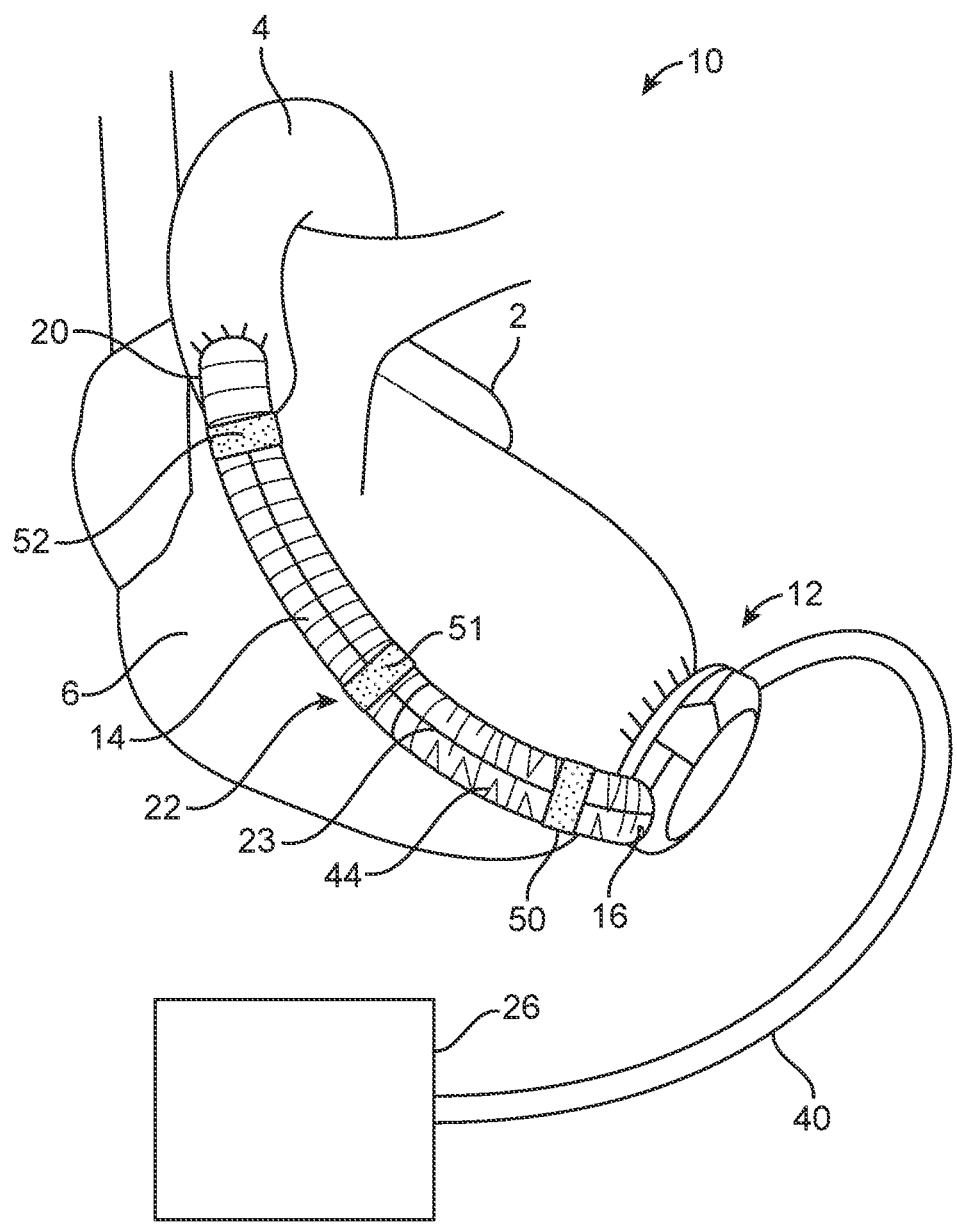
FIG. 2 is a schematic perspective view of a pump, an outflow cannula, one or more electrodes, and a controller of the system of FIG. 1.
Figure 3:
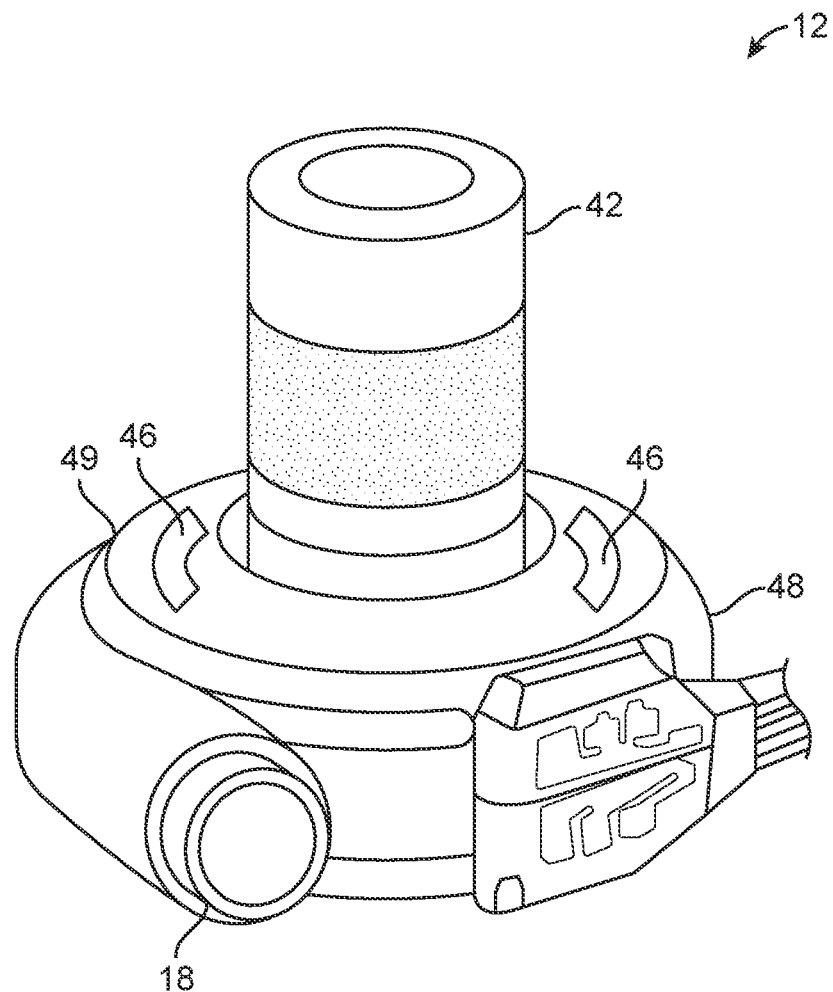
FIG. 3 is a schematic perspective view of the pump of the system of FIG. 1.

FIGS. 1-3 are schematic perspective views of one embodiment of a ventricular assist system 10. The system 10 includes a pump 12 adapted to be connected to a heart 2 of a patient, and an outflow cannula 14 that includes a first end 16 adapted to be connected to an outlet 18 (FIG. 3) of the pump and a second end 20 adapted to be connected to an artery 4 of the patient. The system further includes one or more electrodes 22 disposed on an outer surface 24 of the outflow cannula 14 and adapted to be disposed adjacent to an exterior wall 6 of the heart, and a controller 26 electrically connected to the pump 12 and the electrodes, where the controller is adapted to provide one or more signals to the electrodes.

The system 10 can include any suitable additional elements or components. For example, system 10 includes optional display 28. In one or more embodiments, the display 28 and the controller 26 are integral, i.e., they are disposed within the same housing or case. In the embodiment illustrated in FIG. 1, the display 28 is electrically connected to the controller 26 by a cable 30. The display 28, however, can be connected to the controller 26 using any suitable wired or wireless techniques, e.g., Bluetooth. The system 10 can also include an optional battery 32 that is electrically connected to the controller 26 by a cable 34. In one or more embodiments, the battery 32 can be integral with the controller 26, e.g., the battery can be disposed within a housing 36 of the controller. The system 10 can receive electrical energy from any suitable power source or sources. In one or more embodiments, the system 10 can receive electrical energy from at least one of a wall outlet 38 or the battery 32.

The pump 12 of the system 10 can include any suitable pump or pumps, e.g., an impeller-driven or pneumatic-driven pump providing pulsatile or non-pulsatile flow, an extra-corporeal membrane oxygenation (ECMO) system, an intra-aortic balloon pump, or other mechanical circulatory support device configured to assist the mechanical pumping function of the heart. In one or more embodiments, the pump 12 can include a centrifugal pump. The pump 12 can be electrically connected to the controller 26 using any suitable technique or techniques. In one or more embodiments, the pump 12 is electrically connected to the controller 26 by a driveline 40. In one or more embodiments, the pump 12 can be integral with the controller 26 when the controller is implantable. While the system 10 of FIGS. 1-3 includes a single pump 12, the system can include any suitable number of pumps. In one or more embodiments, the pump 12 can be disposed outside of a body of the patient and connected to the heart using any suitable technique.

The pump 12 includes a housing 48, the inflow cannula 42, and the outlet 18. Further, the pump 12 can be connected to the heart 2 using any suitable technique. For example, the inflow cannula 42 of the pump 12 (FIG. 3) can be connected to any suitable portion of the heart 2 of the patient. In one or more embodiments, the inflow cannula 42 can be connected to a ventricle of the heart 2 using a sewing ring 49 such that the pump is fluidly connected between the ventricle and the artery 4 of the patient.

The outflow cannula 14 of the system 10 can include any suitable conduit or graft that connects the pump 12 to the artery 4 of the patient. In one or more embodiments, the outflow cannula 14 can include a graft. The graft can be anastomosed to the ascending aorta 4 (or other artery) to direct pump outflow into the patient's arterial system. In one or more embodiments, the outflow cannula 14 can be an 8 to 12 mm diameter graft fabricated from a polyester material. The cannula 14 can include a gel-impregnated graft.

The first end 16 of the outflow cannula 14 can be connected to the outlet 18 of the pump 12 using any suitable technique or techniques. Further, the second end 20 of the outflow cannula 14 can be connected to one or more arteries 4 of the heart using any suitable technique or techniques.

Further, the outflow cannula 14 can include a strain relief member 44 that can be adapted to prevent kinking of the cannula. The strain relief member 44 can be disposed over a portion or portions of the outflow cannula 14. In one or more embodiments, the strain relief member 44 can extend from the outlet 18 of the pump 12 exteriorly along at least a portion of the length of the cannula 14. The strain relief member 44 can be formed of a coiled metal or plastic material that provides flexibility of the proximal portion of the cannula 14 to resist kinking of the cannula.

The system 10 further includes the one or more electrodes 22. Such electrodes 22 can be disposed on or in the outflow cannula 14 in any suitable location. In one or more embodiments, at least one electrode 22 is disposed on the outer surface 24 of the outflow cannula 14 using any suitable technique or techniques. The electrodes 22 can be adapted to be disposed adjacent to the exterior wall 6 of the heart 2 as described, e.g., in U.S. Patent Publication No. 2019/0290153 A1 to Zhang and entitled METHOD AND APPARATUS FOR SELECTING A SENSING VECTOR CONFIGURATION IN A MEDICAL DEVICE. As used herein, the term "adjacent to the exterior wall of the heart" means that one or more electrodes 22 are disposed such that they are in contact with the exterior wall 6 of the heart 2 or close enough to the exterior wall such that the electrodes can provide a signal or signals to the heart. In one or more embodiments, one or more of the electrodes 22 can be connected to the exterior wall 6 of the heart 2 using any suitable technique or techniques, e.g., sutures, staples, clips, etc.

The system 10 can include any suitable number of electrodes 22, e.g., one, two, three, four, five, or more electrodes. Further, the electrodes 22 can include any suitable type of electrode, e.g., at least one of a ring, coil, hemispherical, directional, or segmented electrode. In one or more embodiments, each of the electrodes 22 is the same type of electrode. In one or more embodiments, at least one electrode 22 is different from at least one additional electrode.

Further, the electrodes 22 can be adapted to sense or detect electrical signals from the heart or to provide any suitable type of therapy to the heart 2. In one or more embodiments, at least one electrode 22 can be a sensing electrode that can be adapted to detect or sense any suitable electrical signal or signals from the heart 2. Further, at least one electrode 22 can be a pacing electrode that can be adapted to provide a pacing signal or signals to the heart 2. Further, at least one electrode 22 can a defibrillation electrode that can be adapted to provide one or more high voltage stimulation signals to the heart 2. Although described as sensing, pacing, or defibrillation electrodes, one or more electrodes 22 can be adapted to provide several different types of signals to the heart 2. For example, a pacing electrode 22 can be adapted to also sense one or more electrical signals from the heart. Further, in one or more embodiments, such pacing electrode 22 can also be adapted to provide one or more high voltage stimulation signals to the heart 2.

In one or more embodiments, the electrodes 22 can include a pacing electrode 50, a second pacing electrode 51, and a third pacing electrode 52 (collectively referred to herein as electrodes 22). The pacing electrode 50 can be adapted to provide a pacing signal from the controller 26 to the heart 2. The second pacing electrode 51 can be adapted to provide a second pacing signal from the controller 26 to the heart 2. Further, the third pacing electrode 52 can be adapted to provide a third pacing signal from the controller 26 to the heart 2. Although depicted as including three pacing electrodes 50, 51, 52, the system 10 can include any suitable number of pacing electrodes. In addition to the pacing electrodes shown in FIGS. 1-3, the system 10 can include any other suitable types of electrodes, e.g., sensing electrodes, defibrillation electrodes, etc.

The system 10 can also include one or more electrodes disposed on or in the pump 12. For example, as shown in FIG. 3, the pump 12 can include one or more electrodes 46 disposed on its housing 48 or the sewing ring 49 that is utilized to connect the pump to the heart 2. The electrodes 46 can include any suitable type of electrode, e.g., the same types of electrodes described herein in reference to electrodes 22. Further, any suitable number of electrodes 46 can be disposed on the pump 12, e.g., one, two, three, four, five, or more electrodes. The electrodes 46 can include at least one of a sensing, pacing, or defibrillation electrode. In one or more embodiments, at least one of the pacing electrodes 50, 51, 52 can be disposed on the pump 12. Further, each of the electrodes 46 can be electrically connected to the controller 26 using any suitable technique or techniques as is further described herein. In one or more embodiments, at least one of the electrodes 46 can include at least two or more isolated conductive portions that can provide two or more distinct signals to the heart 2. Further, in one or more embodiments, the housing 48 of the pump 12 can function as any suitable electrode described herein.

As mentioned herein, the electrodes 22 can be disposed in any suitable location on or in the outflow cannula 14. In one or more embodiments, the strain relief member 44 can be disposed between one or more electrodes 22 and the outflow cannula 14. For example, as shown in FIGS. 1-2, the pacing electrode 50 can be disposed on the strain relief member 44 using any suitable technique such that the member is disposed between the pacing electrode and the outflow cannula 14.

Electrically connected to the pump 12 and the electrodes 22, 46 is the controller 26. The controller 26 is adapted to provide one or more signals to the electrodes 22, 46 using any suitable pacing or high voltage stimulation vectors. In one or more embodiments, the controller 26 can be adapted to provide one or more control signals to the pump 12 as is further described herein. In one or more embodiments, the controller 26 can obtain cardiac electrical signals corresponding to electrical activity of the heart 2 via one or more sensing vectors that include combinations of electrodes 22 and 46.

The controller 26 can be electrically connected to the pump 12 and the electrodes 22, 46 using any suitable technique, e.g., by the driveline 40, which can extend from within the patient's body to an external controller or be completely disposed within the body for an implanted controller. In the illustrated embodiment, the driveline 40 electrically connects the controller 26 to the pump 12. One or more conductors 23 (FIG. 2) can electrically connect the pump 12 to the electrodes 22. Such conductors 23 can be disposed on the outer surface 24 of the outflow cannula 14 or within the cannula. The conductors 23 can further be adapted to electrically connect the electrodes 22 to the controller 26 using any suitable technique or techniques. In one or more embodiments, the conductors 23 directly connect the electrodes 22 to the controller 26 without electrically connecting such electrodes to the pump 12. In other words, one or more of the conductors 23 can be disposed within the driveline 40 and split from the driveline to the electrodes 22 without first being electrically connected to the pump 12.

Figure 4:
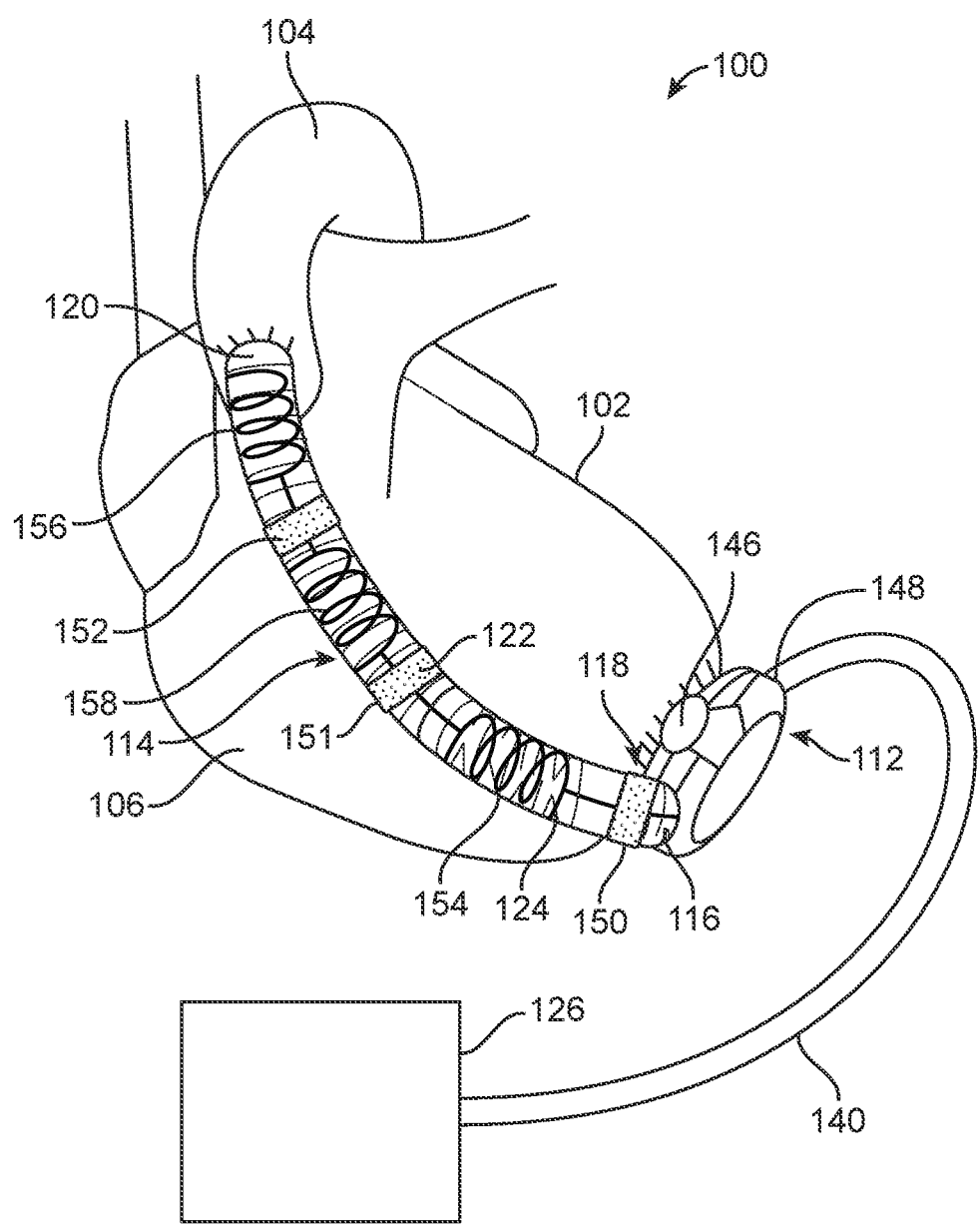
FIG. 4 is a schematic perspective view of another embodiment of a ventricular assist system.

As is also mentioned herein, the various embodiments of ventricular assist systems can include any suitable number and type of electrodes, e.g., sensing, pacing, or defibrillation electrodes. For example, FIG. 4 is a schematic perspective view of a portion of another embodiment of a system 100. All of the design considerations and possibilities regarding the system 10 of FIGS. 1-3 apply equally to the system 100 of FIG. 4. The system 100 includes a pump 112 adapted to be connected to a heart 102 of a patient, and an outflow cannula 114 that includes a first end 116 adapted to be connected to an outlet 118 of the pump and a second end 120 adapted to be connected to an artery 104 of the patient. The system 100 also includes electrodes 122 disposed on an outer surface 124 of the outflow cannula 114 and adapted to be disposed adjacent to an exterior wall 106 of the heart 102. Further, the system includes a controller 126 electrically connected to the pump 112 and the electrodes 122 by driveline 140, where the controller is adapted to provide one or more signals to the electrodes and the pump.

The electrodes 122 can include any suitable electrodes. In the embodiment illustrated in FIG. 4, the electrodes 122 include a first pacing electrode 150, a second pacing electrode 151, and a third pacing electrode 152. The pacing electrodes 150, 151, 152 are adapted to provide one or more pacing signals from the controller 126 to the heart 102 of the patient. In one or more embodiments, the first pacing electrode 150 is adapted to provide a first pacing signal from the controller 126 to the heart 102, the second pacing electrode 151 is adapted to provide a second pacing signal from the controller to the heart, and the third pacing electrode 152 is adapted to provide a third pacing signal from the controller to the heart.

The pacing electrodes 150, 151, 152 can be disposed on the outer surface 124 of the outflow cannula 114 in any suitable location such that are adjacent to the exterior wall 105 of the heart 102. In one or more embodiments, one or more pacing electrodes can be disposed on the pump 112. For example, the second pacing electrode 151 can be disposed on the pump 112, e.g., on a housing 148 of the pump as described regarding electrodes 46 of system 10 of FIGS. 1-3. In one or more embodiments, a fourth pacing electrode 146 can be disposed on the housing 148 of the pump 112.

The electrodes 122 can further include one or more defibrillation electrodes disposed in any suitable location relative to the heart 102 of the patient. For example, system 100 as illustrated in FIG. 4 includes a first defibrillation electrode 154 and a second defibrillation electrode 156. The first and second defibrillation electrodes 154, 156 are each electrically connected to the controller 126 and adapted to provide a high voltage stimulation signal from the controller to the heart 102 of the patient. The first and second defibrillation electrodes 154, 156 can be adapted to be disposed adjacent to the exterior wall 106 of the heart 102. In one or more embodiments, the first defibrillation electrode 154 can be disposed on the outer surface 124 of the outflow cannula 114, and the second defibrillation electrode 156 can be disposed on either the outer surface of the outflow cannula or the pump 112. As illustrated in FIG. 4, the second defibrillation electrode 156 is disposed on the outer surface 124 of the outflow cannula 114.

In one or more embodiments, the system 100 can include a third defibrillation electrode 158 disposed in any suitable location relative to the cannula 114 and the pump 112. The third defibrillation electrode 158 can include any suitable electrode and be adapted to provide any suitable signal to the heart 102. Further, the third defibrillation electrode 158 can be adapted to be disposed adjacent to the heart 102.

As mentioned herein, controller 126 can provide one or more therapies to the heart 102 using any suitable technique or vector. In one or more embodiments, the controller 126 can be adapted to provide at least one of a ventricular pacing therapy, an anti-tachycardia pacing (ATP) therapy, or a defibrillation therapy. Any suitable combination of electrodes 122, 146 can be utilized to provide one or more therapies. In one or more embodiments, a vector for ventricular or ATP pacing therapy can include electrical signals being provided to the heart 102 by the second pacing electrode 151 and the third pacing electrode 152, by the first pacing electrode 150 and the first defibrillation electrode 154, or by the third defibrillation electrode 158 and the first defibrillation electrode. In one or more embodiments, a second vector for ventricular or ATP pacing therapy can include electrical signals being provided to the heart 102 by the fourth pacing electrode 146 disposed on the housing 148 of pump 112 (e.g., electrodes 46 of FIG. 3) and the first pacing electrode 150, by the fourth pacing electrode and the second pacing electrode 151, or by the fourth pacing electrode and the third pacing electrode 152. In one or more embodiments, a third vector for ventricular or ATP pacing therapy can include electrical signals being provided to the heart 102 by the fourth pacing electrode 146 and the first defibrillation electrode 154, by the fourth pacing electrode and the third defibrillation electrode 158, or by the fourth pacing electrode and the first defibrillation electrode 154. Other vectors that can be utilized with controller 126 are described, e.g., in U.S. Patent Publication No. 2019/0336767 A1 to Klepfer et al. and entitled MODE OF OPERATION FOR AN IMPLANTABLE CARDIAC RHYTHM MANAGEMENT DEVICE CO-IMPLANTED WITH A VENTRICULAR ASSIST DEVICE.

Further, the controller 126 can provide one or more defibrillation therapies to the heart 102 using one or more vectors. Any suitable combination of electrodes 122, 146 can be utilized to provide these therapies. In one or more embodiments, one or more vectors can include high voltage stimulation signals provided by the third defibrillation electrode 158 and the housing 148 of the pump 112 (which includes a defibrillation electrode in place of or in addition to the fourth sensing electrode 146), by the first defibrillation electrode 154 and the housing, or by the third defibrillation electrode, the second defibrillation electrode 156, and the housing.

In one or more embodiments, the controller 126 can be adapted to provide one or more control signals to the pump 112 as is described, e.g., in U.S. Patent Publication No. 2019/0336767 A1. In one or more embodiments, the controller 126 can obtain cardiac electrical signals corresponding to electrical activity of the heart 2 via one or more sensing vectors that include combinations of electrodes 122 and 146.

Figure 5:
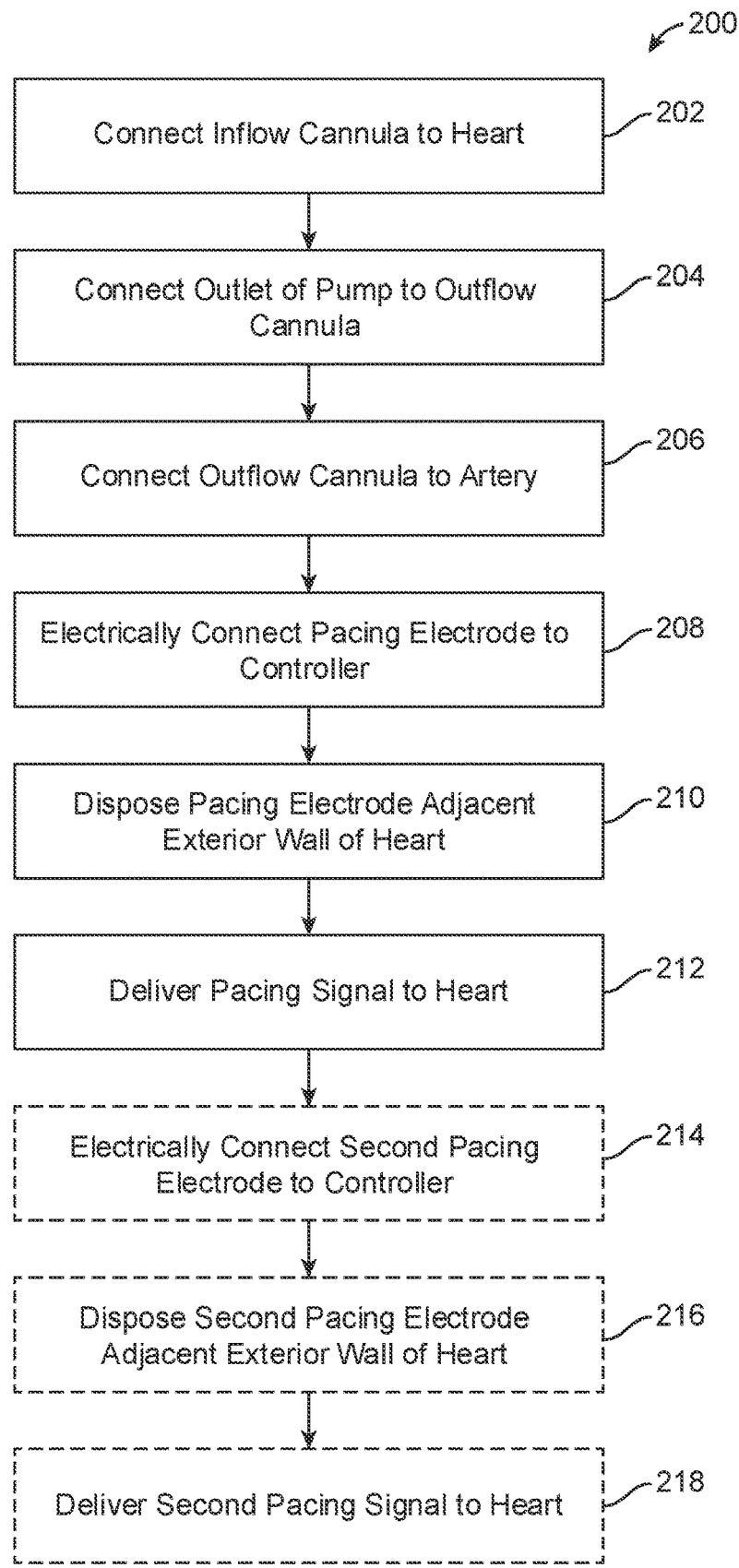
FIG. 5 is a flowchart of a method of using the system of FIG. 1.

As mentioned herein, any suitable technique can be utilized with the various embodiments of ventricular assist systems for implantation and therapy delivery. For example, FIG. 5 is a flowchart of one embodiment of a method 200 of utilizing ventricular assist system 10 of FIGS. 1-3. Although described in reference to system 10, the method 200 can be utilized with any suitable system, e.g., system 100 of FIG. 4. At 202, the inflow cannula 42 of the pump 12 can be connected to a portion of the heart 2 of the patient. The outlet 18 of the pump 12 can be connected to the outflow cannula 14 at 204. The outflow cannula 14 can be connected to the artery 4 of the patient at 206. At 208, the electrodes 22 such as pacing electrode 50 that is disposed on the outer surface 24 of the outflow cannula 14 can be electrically connected to the controller 26. In one or more embodiments, conductors 23 can be disposed on or within the outflow cannula 14 and electrically connect the electrodes 22 to the pump 12 or to the controller 26 through driveline 40.

At 210, the pacing electrode 50 can be disposed adjacent to the exterior wall 6 of the heart 2 of the patient. In one or more embodiments, the pacing electrode 50 can be disposed such that it is in contact with the heart 2. Further, at 212 a pacing signal can be delivered from the controller 26 to the heart 2 of the patient utilizing the pacing electrode 50 and the controller. Any suitable pacing signal can be provided. In one or more embodiments, a high voltage stimulation signal can be provided to the heart 2 by the pacing electrode 50.

In one or more embodiments, a second pacing electrode 51 disposed on the outer surface 24 of the outflow cannula 14 can be electrically connected to the controller 26 at 214. Further, at 216, the second pacing electrode 51 can be disposed adjacent to the exterior wall 6 of the heart 2 of the patient. In one or more embodiments, the second pacing electrode 51 can be disposed such that it is in contact with the exterior wall 6 of the heart 2. Further, at 218, a second pacing signal can be delivered to the heart of the patient utilizing the second pacing electrode 51 and the controller 26.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A ventricular assist system comprising:
a pump adapted to be connected to a heart of a patient;
an outflow cannula comprising a first end adapted to be connected to an outlet of the pump and a second end adapted to be connected to an artery of the patient;
a plurality of pacing electrodes disposed on an outer surface of the outflow cannula and adapted to be disposed adjacent to an exterior wall of the heart; and
a controller electrically connected to the pump and the plurality of pacing electrodes, wherein the controller is adapted to provide a pacing signal to the heart of the patient via the plurality of pacing electrodes.

2. The system of claim 1, wherein the plurality of pacing electrodes is adapted to provide the pacing signal from the controller to the heart of the patient.

3. The system of claim 1, further comprising a pump electrode disposed on the pump and adapted to be disposed adjacent to the exterior wall of the heart, wherein the pump electrode comprises at least one of a sensing, a pacing, or a defibrillation electrode.

4. The system of claim 1, wherein the pacing signal comprises a first pacing signal, wherein a first pacing electrode of the plurality of pacing electrodes is adapted to provide the first pacing signal, and wherein a second pacing electrode of the plurality of pacing electrodes is adapted to provide a second pacing signal from the controller to the heart of the patient.

5. The system of claim 1, wherein the outflow cannula comprises a graft.

6. The system of claim 5, wherein the graft comprises a gel-impregnated graft.

7. The system of claim 1, further comprising a first defibrillation electrode disposed on the outer surface of the outflow cannula and a second defibrillation electrode disposed on either the outer surface of the outflow cannula or the pump, wherein the first and second defibrillation electrodes are adapted to be disposed adjacent to the exterior wall of the heart, wherein the first and second defibrillation electrodes are electrically connected to the controller and adapted to provide a defibrillation signal from the controller to the heart of the patient.

8. The system of claim 1, wherein the pump is adapted to be connected to a ventricle of a patient.

9. The system of claim 1, wherein the controller is configured to select different pacing electrodes of the plurality of pacing electrodes to deliver pacing signals having different pacing vectors to the heart.

10. A method comprising:
connecting an inflow cannula of a pump to a portion of a heart of a patient;
connecting an outlet of the pump to an outflow cannula;
connecting the outflow cannula to an artery of the patient;
electrically connecting a plurality of pacing electrodes disposed on an outer surface of the outflow cannula to a controller;

disposing the plurality of pacing electrodes adjacent to an exterior wall of the heart of the patient; and delivering a pacing signal from the controller to the heart of the patient utilizing the plurality of pacing electrodes.

11. The method of claim 10, wherein delivering the pacing signal comprises delivering a first pacing signal utilizing at least a first electrode of the plurality of pacing electrodes, and wherein the method further comprises:

delivering a second pacing signal from the controller to the heart of the patient utilizing at least a second pacing electrode of the plurality of pacing electrodes.

12. The method of claim 10, wherein delivering the pacing signal from the controller to the heart of the patient utilizing the plurality of electrodes comprises:

selecting different pacing electrodes of the plurality of pacing electrodes to deliver pacing signals having different pacing vectors to the heart of the patient.

13. An outflow cannula for a ventricular assist system, the outflow cannula comprising:

a first end adapted to be connected to an outlet of a pump of the ventricular assist system and a second end adapted to be connected to an artery of a patient;

first and second pacing electrodes disposed on an outer surface of the outflow cannula and adapted to be disposed adjacent to an exterior wall of the heart, wherein each of the first and second pacing electrodes are adapted to be electrically connected to a controller, wherein the first pacing electrode is adapted to deliver a first pacing signal from the controller to the heart and the second pacing electrode is adapted to deliver a second pacing signal from the controller to the heart; and a conductor disposed on the outer surface of the outflow cannula or within the outflow cannula and adapted to electrically connect the first and second pacing electrodes to the controller.

14. The outflow cannula of claim 13, wherein each of the first and second pacing electrodes comprises a ring electrode or a coil electrode.

15. The outflow cannula of claim 13, further comprising a third pacing electrode that is adapted to be connected to be electrically connected to the controller and deliver a third pacing signal from the controller to the heart.

16. The outflow cannula of claim 15, wherein the third pacing electrode is disposed on the outer surface of the outflow cannula and adapted to be disposed adjacent to the exterior wall of the heart.

17. The outflow cannula of claim 15, wherein the third pacing electrode is disposed on the pump and adapted to be disposed adjacent to the exterior wall of the heart.

18. The outflow cannula of claim 13, further comprising a strain relief member disposed over a portion of the outflow cannula.

19. The outflow cannula of claim 18, wherein a portion of the strain relief member is disposed between at least one of the first pacing electrode, the second pacing electrode, or a third pacing electrode and the outflow cannula.

20. The outflow cannula of claim 13, further comprising a first defibrillation electrode disposed on the outer surface of the outflow cannula and a second defibrillation electrode disposed on either the outer surface of the outflow cannula or the pump, wherein the first and second defibrillation electrodes are adapted to be disposed adjacent to the exterior wall of the heart, wherein the first and second defibrillation electrodes are adapted to be electrically connected to the controller and provide a defibrillation signal from the controller to the heart of the patient.

* * * * *